United States Patent [19]
Rashid et al.

[11] Patent Number: 5,750,143
[45] Date of Patent: May 12, 1998

[54] CONTROLLED RELEASE DEVICE

[75] Inventors: Abdul Rashid, Glasgow; Howard Norman Ernest Stevens, Drymen; Julie Stephanie Binns, Glasgow, all of United Kingdom; James Leonard Mackie, Windsor, Canada

[73] Assignee: R.P. Scherer Corporation, Troy, Mich.

[21] Appl. No.: 424,377

[22] PCT Filed: Nov. 4, 1993

[86] PCT No.: PCT/GB93/02271

§ 371 Date: Jun. 27, 1995

§ 102(e) Date: Jun. 27, 1995

[87] PCT Pub. No.: WO94/09746

PCT Pub. Date: May 11, 1994

[30] Foreign Application Priority Data

Nov. 4, 1992 [GB] United Kingdom ............ 9223144

[51] Int. Cl.$^6$ .............................. A61K 9/48; A61K 9/52
[52] U.S. Cl. .................... 424/451; 424/452; 424/453; 424/454; 424/457; 424/463
[58] Field of Search ........................ 424/451, 454, 424/457, 453, 456, 452, 463

[56] References Cited

U.S. PATENT DOCUMENTS

| | | | |
|---|---|---|---|
| 3,823,843 | 7/1974 | Stephens et al. | 220/42 A |
| 4,487,327 | 12/1984 | Grayson | 220/8 |
| 4,667,498 | 5/1987 | Sauter | 72/108 |
| 5,387,421 | 2/1995 | Amidon et al. | 424/453 |

FOREIGN PATENT DOCUMENTS

| | | |
|---|---|---|
| 0246804 | 5/1987 | European Pat. Off. . |
| 2232236 | 1/1974 | Germany . |
| 2148235 | 5/1985 | United Kingdom . |

Primary Examiner—James M. Spear
Attorney, Agent, or Firm—Gifford, Krass, Groh, Sprinkle, Patmore, Anderson & Citkowski, P.C.

[57] ABSTRACT

A controlled release capsule comprises a male plug (2) formed of a water-swellable hydrogel which is engaged with a neck portion (4) of a female body (6). The capsule is intended to deliver two dosages of pharmaceutically active material at different times. A water soluble cap (8) is fitted over mouth (14) of the body, and defines a first volume (9) containing a first unit dosage (10). A second unit dosage (12) is contained within a second volume (11) defined by the plug and the female body. When the capsule is swallowed by a patient, the cap dissolves quickly in the aqueous medium within the gastro-intestinal tract and releases the first dosage. The aqueous medium then comes into contact with the hydrogel plug which swells and becomes disengaged from the body, usually in the intestine, thereby releasing the second dosage a predetermined time after the first dosage.

12 Claims, 2 Drawing Sheets

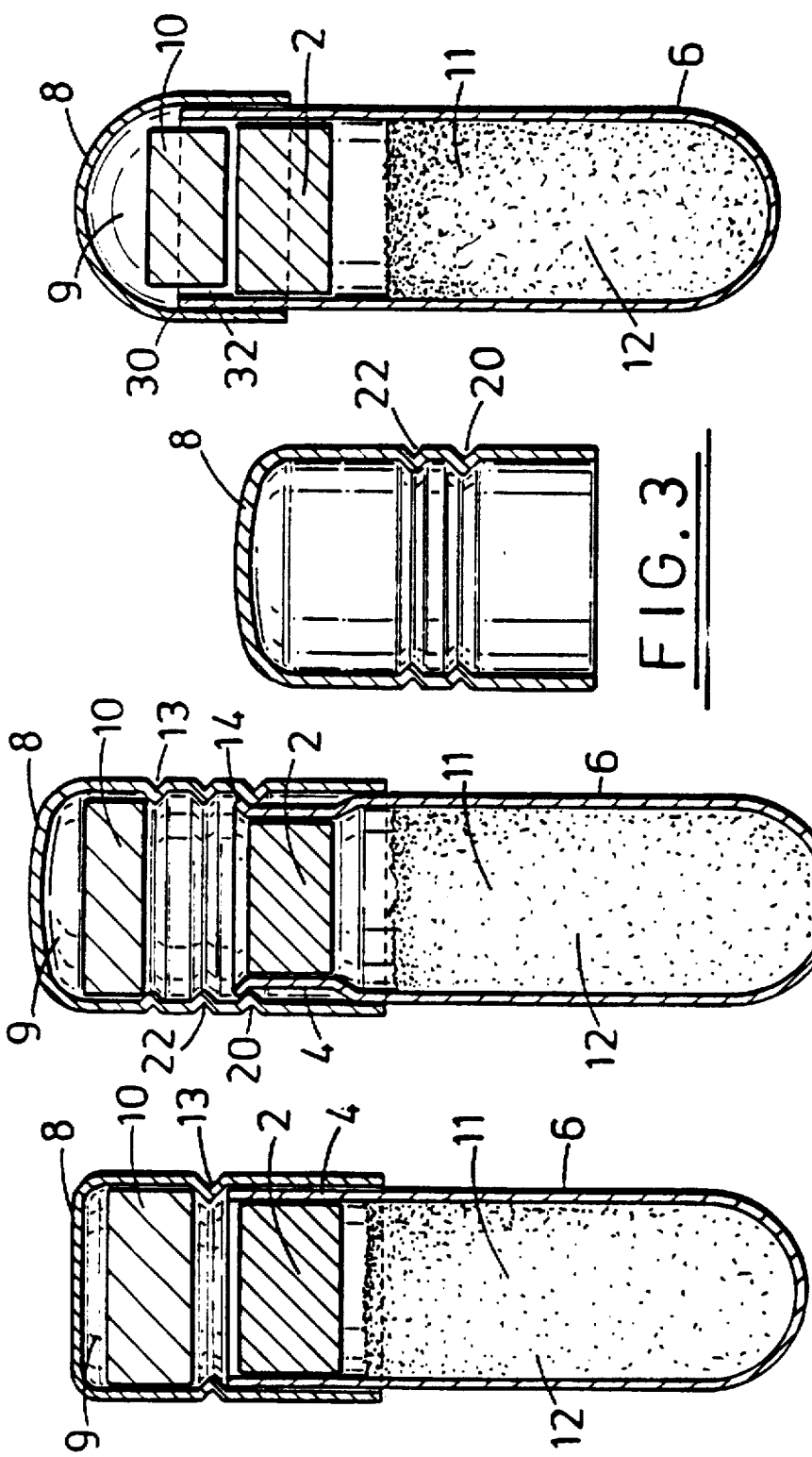

CONTROLLED RELEASE DEVICE

This application is a 371 of PCT/GB93/02271 filed Nov. 4, 1993.

TECHNICAL FIELD

The present invention relates to a controlled release capsule construction which comprises a male member engaged within a neck portion of a female body; the capsule including a water swellable material which swells so as to disengage the female body upon exposure of the capsule to an aqueous medium. The capsule is intended to release two dosages of pharmaceutically active materials at different times.

BACKGROUND

International patent specification WO90/09168 discloses a device of this type which comprises a water swellable male plug engaged within a female body. A pharmaceutically active material is contained within the device. When the capsule is exposed to water, the male hydrogel plug swells and eventually disengages itself from the female body, thereby allowing the pharmaceutically active material contained within the device to be released. It has been found that the time taken to release the pharmaceutical material is predictable and reproducible, so that the device may be used to release pharmaceutically active material within the body of a patient after a predetermined time interval (e.g. 0.5 to 12 hours). This may, for example, be useful in the treatment of medical conditions where it is desirable to administer a pharmaceutically active material to the patient sometime through the night while the patient is asleep, so as to provide a desired level of the drug in the patient in accordance with his needs, for example during the night or when he awakes. It may also be useful to allow dosing of materials at a predetermined point as the capsule passes through the gastro-intestinal tract, for example in the colon.

Patent specification WO92/13521 (Alza Corporation) describes fluid-imbibing dispensing devices for delayed delivery of a pharmaceutically active agent, which include an expansion means which absorbs fluid from a surrounding environment. The dispensing device comprises a housing having first and second wall sections telescopically engaged with each other, particularly a capsule having a hollow cap and a hollow body; either the cap or the body is in the form of a male section fitted inside the open end of the other female section. The expansion means is contained within the device and expands as it absorbs fluid, forcing apart the two sections of the device. The expansion means may be a swellable polymer or an osmotic formulation which swells as it absorbs fluid. In order to allow fluid to come into contact with the expansion means contained within the device, one of the wall sections adjacent to the expansion means is fluid-permeable. After the sections are disengaged, fluid enters the device and comes into contact with the active agent contained within the device, thereby dispensing the active agent into the fluid.

Conventional hard gelatin capsules are produced and filled in large numbers using high speed automatic machinery. Very often, the cap is prefitted to the capsule body during manufacture of the capsule. During filling, the filling machine removes the cap, fills the capsule with pharmaceutical material, and then replaces the cap in a manner such that the cap is locked onto the capsule body. Patent specification U.S. Pat. No. 3,399,803 discloses a self-locking medicament capsule wherein the body has a groove near its open end and the cap has a corresponding ridge which snaps into the groove so as to lock the cap and body together. U.S. Pat. No. 4,442,941 discloses a bayonnet-type arrangement whereby a raised portion on the cap is engaged into a groove on the body. European patent specification 246504 also discloses a capsule body having a groove near its mouth for the purposes of preventing the capsule distorting from its cylindrical form, which may cause difficulty in fitting the cap onto the capsule body.

SUMMARY OF THE INVENTION

The present invention relates to a development of the capsule construction disclosed in WO90/09168 to allow sequential dosing of a patient at different times with the same or different pharmaceutically active materials.

Thus, the present invention provides a controlled release capsule which comprises a male member engaged within a female body;

the capsule including a water swellable material which swells so as to disengage the female body upon exposure of the capsule to an aqueous medium;

a cap of a water soluble material being fitted over a mouth of the female body and enclosing the male member such as to define a first volume containing a first unit dosage of a pharmaceutically active material; and the female body and the male member defining a second volume containing a second unit dosage of a pharmaceutically active material.

In a preferred embodiment, the male member is a plug formed of said water-swellable material, such that as the plug swells it disengages from the female body. The plug is preferably formed of a water-swellable hydrogel, such as described in WO90/09168.

In view of the water-soluble nature of the cap (which is for example, formed of gelatin), the cap tends to dissolve very soon after administration to the patient thereby releasing the first dosage of pharmaceutically active material, usually in the patient's stomach. The first dosage of active material may thus become absorbed in the intestine.

Following dissolution of the cap, the hydrogel plug becomes exposed to the aqueous environment and begins to swell. After a predetermined time interval, the hydrogel plug becomes disengaged, thereby releasing the second dosage of pharmaceutically active material at a further predetermined position in the patient's gastro-intestinal tract, such as the colon.

In an alternative embodiment, the water-soluble cap (and usually the capsule body also) is enteric coated so as to resist the acidic pH in the stomach and pass into the intestine. At the higher intestinal pH the enteric coat dissolves and allows dissolution of the cap and release of the first dosage of active material. The plug then hydrates and is expelled after a predetermined time (e.g. in the colon) to release the second dosage of active material.

For convenience, the first and second dosages of pharmaceutically active material are generally provided in solid form, such as a tablet; though other known dosage forms are possible, such as powders, granules, pellets, capsules and semi-solid material. The doses may be of the same or different active material. The first active material may be cast (e.g. as a molten liquid) into the end of the cap.

Although conventionally shaped round caps may be used, the cap is preferably substantially flattened compared to conventional caps so as to accommodate a tablet whilst retaining the compact nature of the capsule by minimising dead space in the first volume. The flattened cap shape also reduces nesting and interlocking between free caps stored together in a filling machine. Interlocking is further minimised by making the caps thicker than conventional, or by enlarging the domed end of the cap. In addition, inwardly extending protrusions may be provided around the inside of the cap, so that a tablet can be clipped into place within the cap and retained there during assembly of the capsule. Such inward protrusions also function to act as stops limiting the extent to which the cap can be pushed onto the capsule body.

In one embodiment of the invention, the hydrogel plug is recessed below the mouth of the female body, so as to provide a location to at least partially receive the first dosage of active material.

The walls of the female body may be formed from a wide variety of materials. They may be of homogenous constructions or they may be laminated. Examples of materials suitable for use in the construction of the body include polyethylene, polypropylene, poly(methylmethacrylate), polyvinyl chloride, polystyrene, polyurethanes, polytetrafluoroethylene, nylons, polyformaldehydes, polyesters, cellulose acetate and nitro cellulose.

However, a preferred construction uses an impermeable coating to cover the exterior of a body which has been formed from a water soluble material. The coating may conveniently be formed by dipping the body in a solution of a material which forms a layer which is impermeable to water. Alternatively, the body might be spray-coated. A preferred class of capsule bodies are conventional hard gelatin or starch capsule bodies coated with a solution of polyvinyl chloride or a polyvinyl acetate copolymer or an ethyl cellulose solution.

If desired, the female body may be provided with a groove adjacent its mouth which co-operates with a corresponding protrusion (for example, a ridge) on the cap so as to prelock or lock the cap and body together in the manner described in the prior art. In a particularly preferred embodiment, the groove is extended so as to form a narrowed neck portion, and the cap is provided with a pre-lock protrusion (for example, a ridge) and a spaced final lock protrusion (for example a ridge), both of which engage with the neck portion during final locking of the capsule cap to the body. The term pre-lock and lock are relative terms which express the degree of difficulty involved in removing the cap from the body. A prelocked cap can be readily removed for future filling of the capsule. A locked cap is not intended to be removed. A protrusion intended for prelocking will generally not extend as far into the groove as a protrusion intended for locking the cap to the body.

Another aspect of the invention relates to a process of filling the capsule, which comprises storing caps and bodies separately, introducing the second dosage into a body, inserting a male plug into a neck of the body, introducing the first dosage above the plug or into a cap, and fitting the cap over the mouth of the body.

In another embodiment, the male member is a hollow member closed at one end, whose opposite open end engages within a neck of the female body. A water swellable material is provided within the capsule which serves to disengage the female body after a predetermined time, by forcing the male member and the female body apart as the material swells in the presence of water. The swellable material inside the capsule may be an osmagent or an osmopolyer. Such an arrangement is disclosed in WO92/13521. In order to allow water to enter the capsule and to contact the water-swellable material a portion of the wall of the capsule adjacent thereto is preferably semipermeable; that is to say it is permeable to the passage of water into the capsule but impermeable to release of other substances from within the capsule.

DETAILED DESCRIPTION OF PREFERRED EMBODIMENTS

Embodiments of the present invention will now be described by way of example only in conjunction with the drawings wherein;

BRIEF DESCRIPTION OF THE DRAWINGS

FIG. 1 is a cross sectional elevation of a first embodiment; and

FIG. 2 is a cross sectional elevation of a second embodiment having prelock and locking ridges in the inside of the cap;

FIG. 3 is a cross-sectional elevation of an alternative cap for the second embodiment;

FIG. 4 is a cross-section of a fourth embodiment; and

Figure 5:
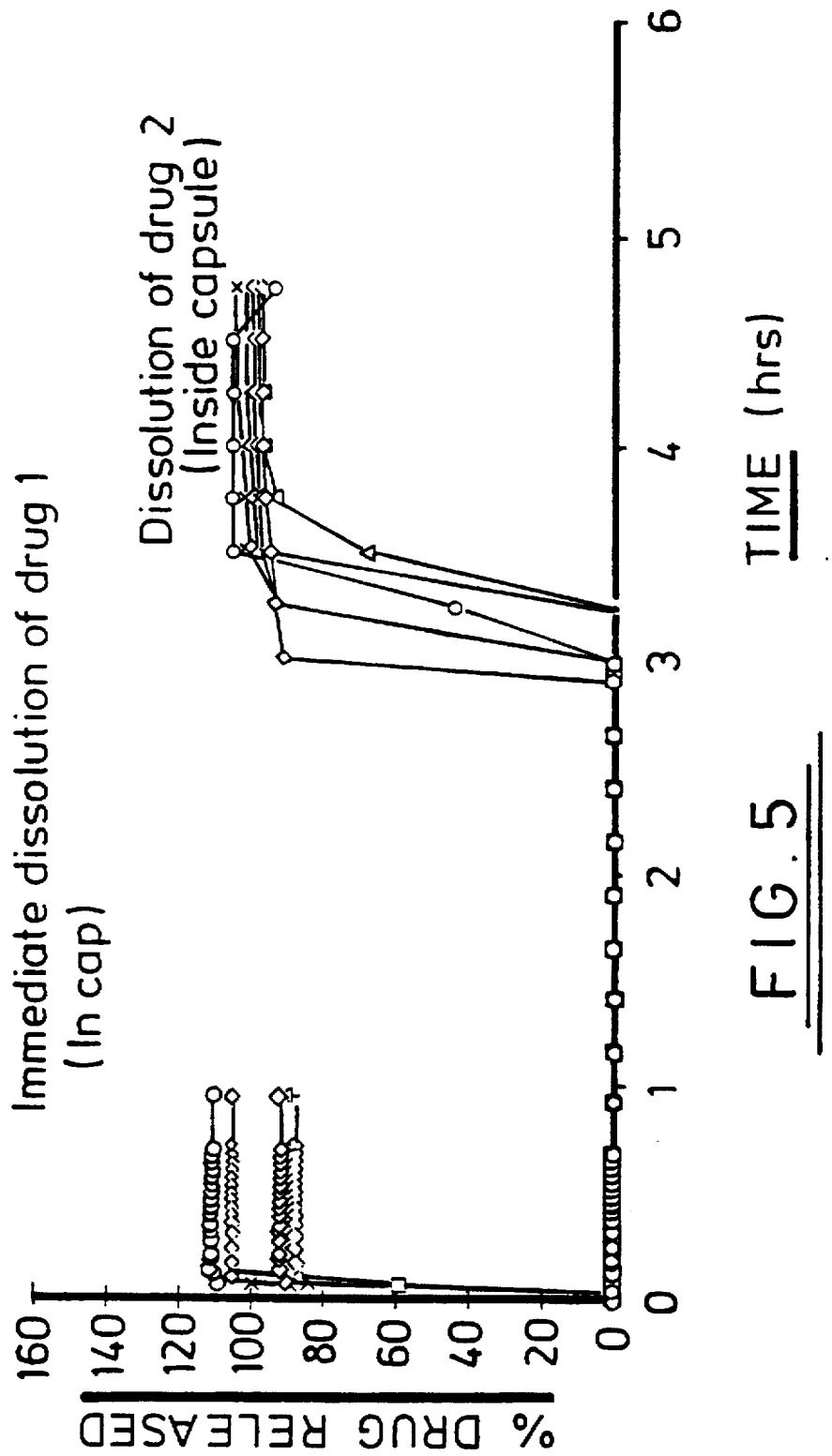
FIG. 5 shows drug release profiles.

The capsule shown in FIG. 1 comprises a male plug 2 formed of a hydrogel material inserted in neck 4 of female body 6. The capsule is closed with a cap 8.

The cap 8 is provided with a substantially flattened top so as to accommodate a first dosage 10 in tablet form in a first volume 9, and to minimise nesting together of caps when stacked in a filling machine. The tablet 10 is retained in the cap by means of an inwardly extending annular protrusion (or series of protrusions) 13 behind which the tablet may be clipped for ease of assembly.

The second dosage of pharmaceutically active material 12 is contained within a second volume 11 in the capsule body and may be in any suitable dosage form, such as powder, granules, tablet or even liquid form. Suitable active materials for use as the first or second active material are disclosed (but not limited to) those given in WO90/09168.

The cap is formed of a water-soluble material, such as gelatin. The capsule body is formed of a water-insoluble material, which may be a water-insoluble plastics material or may be a soluble material coated with a water-impermeable coating.

The capsule body is formed in conventional manner by dipping a mould into a gelatin solution and allowing to dry. The gelatin is then coated with a water-impermeable coating (e.g. by dip coating), after the capsule body has been stripped from the mould pin and trimmed to size. Alternatively, the water-impermeable coating may be applied by spray coating or vapour deposition onto the capsule body. The cap 8 is temporarily fitted over the capsule body. The pre-assembled empty capsule is then stored for later filling. During filling, the cap is removed from the capsule body. A first dosage 10 in tablet form is inserted into first volume 9 in the cap, and a second dosage 12 of a pharmaceutically active material is filled into second volume 11 of the capsule body. The hydrogel plug is then fitted into the neck of the body so that it is just recessed below the top of the neck. Finally, the cap is replaced over the mouth of the capsule body and pushed down. The cap may be sealed in place by known means e.g. by adhesive or sealing strip.

However, the preassembly step is not essential. The caps and bodies may be stored separately and fed separately to the filling machine, particularly if precautions are taken to prevent the caps nesting together and the bodies nesting together during storage and feeding in the filling machine.

When the capsule is administered to a patient, the aqueous environment in the gastro-intestinal tract dissolves the water-soluble cap, and releases the tablet 10 which quickly dissolves thereby administering the drug in the stomach. Since the hydrogel plug is now exposed, it absorbs water and swells, before being expelled from the body after a predetermined time interval (for example 2 to 10 hours). The second pharmaceutical material is then released into the patient's gastro-intestinal tract where it can be absorbed, for example into the colon. The active material which is released into the stomach is one which is suitable for oral administration and is capable of surviving the conditions prevailing in the stomach and intestine. On the other hand, the second pharmaceutically active material is generally one which is unable to survive the stomach/intestine environment and might for example be a protein or other material which would be degraded in the upper part of gastrointestinal tract.

Alternatively a second dose of the same drug may be required at a later time or at a later site of absorption within the gastro-intestinal tract.

FIG. 2 shows a second embodiment which is similar to the first, except that the cap is provided with a prelock ring 20 and a lock ring 22 (in addition to the protrusion/stop 13). The capsule body is provided with a substantially cylindrical neck portion 4 and a flared mouth portion 14 into which the rings 20 and 22 may become clipped.

During manufacture, the cap is prelocked to the body by pressing the cap downwards until prelock ring 20 engages over flared mouth 14. When the capsule is subsequently filled, the cap is removed by the filling machinery and the tablet 10 clipped behind inwardly protruding ring 13. The capsule body is then filled with the second pharmaceutically active material 12 prior to insertion of the hydrogel plug 2. The cap with retained tablet 10 is then pushed over the mouth of the capsule body so that both prelock ring 20 and locking ring 22 clip over the flared mouth 14 of the body and lie within the cylindrical neck portion 4 of the capsule body. Protruding ring 13 acts as stop to prevent the cap being pushed too far down onto the body (as does the lower shoulder of the neck portion 4).

FIG. 3 shows an alternative cap for the second embodiment in which the stop ring 13 is omitted.

FIG. 4 shows a third embodiment (analogous parts having the same reference number) wherein the plug 2 is recessed below the level of the mouth 30 of the body 6 so as to provide a location 32 to receive the tablet 10. The cap and body may optionally be provided with prelock and locking rings as shown in FIGS. 2 or 3 to hold the cap in place, or the cap may be held on in other known manner.

EXAMPLE 1

A capsule as shown in FIG. 2 was filled with two drugs and the release profiles assessed. An 800mg tablet (diameter 6.6mm) containing 10mg promethazine hydrochloride (first drug) was placed inside the gelatin cap. 10mg of neat metoclopramide (second drug) powder was placed in the coated gelatin capsule, and the capsule closed with a hydrogel plug recessed below the level of the capsule top. The cap was placed over the capsule and locked in place. The closed capsule was then placed in water and the amount of drug released was monitored spectrophotometrically.

The capsule details and results are given in the Table.

EXAMPLE 2

The procedure of Example 1 was repeated except that the first drug placed in the cap was 10mg of neat metoclopramide; and the second drug in the capsule body was an 800mg tablet (diameter 6.6mm) containing 10mg promethazine hydrochloride.

The capsule details and results are given in the Table. The release profiles of the two drugs are shown in FIG. 5.

TABLE

| Example | First drug mean release time hrs. | Second Drug mean release time hrs. |
| --- | --- | --- |
| 1 | 0.25 (86%) | 2.75 (87%) |
| 2 | immediate (99%) | 3.3 (101%) |

Plug length = 4 mm
Plug diameter = 6.90 mm
Plug recess = 0.50 mm
Figures in brackets give the percentage of drug released.

We claim:

1. A controlled release capsule which comprises a male plug engaged within a female body;

the plug being formed of a water swellable material which swells so as to disengage the female body upon exposure of the capsule to an aqueous medium;

a cap of a water soluble material fitted over a mouth of the female body and enclosing the male plug such as to define a first containing a first unit dosage of a pharmaceutically active material; and the female body and the male plug defining a second volume containing a second unit dosage of a pharmaceutically active material;

wherein the cap and the female body are provided with cooperating pre-lock means to removeably attach the cap to the female body.

2. A capsule according to claim 1 wherein the plug is recessed below the mouth of the female body to least partially define the first volume.

3. A capsule according to claim 1 wherein the co-operating pre-lock means comprises a groove adjacent the mouth of the female body, and a pre-lock protrusion provided on the cap which removably engages the groove for removably attaching the cap to the female body.

4. A capsule according to claim 1 which further comprises co-operating lock means on the cap and body for locking the cap to the body.

5. A capsule according to claim 4 wherein the co-operating lock means comprises a groove adjacent the mouth of the female body, and a locking protrusion provided on the cap which lockably engages the groove for removably attaching the cap to the body.

6. A capsule according to claim 1 wherein the female body further comprises a narrowed neck portion adjacent the mouth of the body, the neck portion being narrower than the mouth and being narrower than the remainder of the body; the cap further comprising an open end, a prelock protrusion adjacent said open end which engages into the neck portion during prelocking, and a locking protrusion spaced from the open end such that said prelock protrusion is disposed between said open end and said locking protrusion, said locking protrusion also engaging into the neck portion as the cap is locked to the body.

7. A capsule cap according to claim 6 wherein the cap further comprises a stop protrusion spaced from said open end such that said locking protrusion is disposed between said prelock protrusion and said locking protrusion, said stop protrusion for preventing the cap being pushed too far onto the female body.

8. A capsule according to claim 1 wherein the cap has a flattened top portion.

9. A capsule according to claim 1 wherein the cap has a thickness such that the cap is unable to nest with other such caps during assembly of the capsule.

10. A capsule according to claim 1 wherein the cap is enteric coated such that when the capsule is swallowed by a patient the cap dissolves and releases the first active material in the intestine of the patient.

11. A controlled release capsule which comprises a male plug engaged within a female body;

the capsule formed of a water swellable material which swells so as to disengage the female body upon exposure of the capsule to an aqueous medium;

a cap of a water soluable material fitted over a mouth of the female body and enclosing the male plug such as to define a first volume containing a first unit dosage of a pharmaceutically active material; and the female body and the male plug defining a second volume containing a second unit dosage of a pharmaceutically active material, wherein the cap is enteric coated such that when the capsule is swallowed by a patient the cap dissolves and releases the first active material in the intestine of the patient.

12. A controlled release capsule which comprises a male plug engaged within a female body;

the capsule formed of a water swellable material which swells so as to disengage female body upon exposure of the capsule to an aqueous medium;

a cap of a water soluble material fitted over a mouth of the female body and enclosing the male plug such as to define a first volume containing a first unit dosage of a pharmaceutically active material; and the female body and the male plug defining a second volume containing a second unit dosage of a pharmaceutically active material, wherein the plug is recessed below the mouth of the female body to at least partially define the first volume.

* * * * *